United States Patent [19]
Shiber

[11] Patent Number: 5,334,211
[45] Date of Patent: * Aug. 2, 1994

[54] LUMEN TRACKING ATHERECTOMY SYSTEM

[75] Inventor: Samuel Shiber, Atkinson, N.H.

[73] Assignee: Surgical System & Instruments, Inc., Atkinson, N.H.

[*] Notice: The portion of the term of this patent subsequent to Mar. 22, 2005 has been disclaimed.

[21] Appl. No.: 913,231

[22] Filed: Jul. 14, 1992

Related U.S. Application Data

[63] Continuation-in-part of Ser. No. 662,558, Feb. 28, 1991, which is a continuation-in-part of Ser. No. 499,726, Mar. 27, 1990, Pat. No. 5,135,531, which is a continuation-in-part of Ser. No. 350,020, May 12, 1989, Pat. No. 4,979,939, which is a continuation-in-part of Ser. No. 326,967, Mar. 22, 1989, Pat. No. 4,957,482, Ser. No. 324,616, Mar. 16, 1989, Pat. No. 5,007,896, Ser. No. 323,328, Mar. 13, 1989, Pat. No. 5,002,553, and Ser. No. 332,497, Apr. 3, 1989, Pat. No. 5,024,651, said Ser. No. 326,967, Ser. No. 324,616, Ser. No. 323,328, and Ser. No. 332,497, each is a continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 225,880, Jul. 29, 1988, Pat. No. 4,842,579, Ser. No. 205,479, Jun. 13, 1988, Pat. No. 4,883,458, and Ser. No. 78,042, Jul. 27, 1987, Pat. No. 4,819,634, said Ser. No. 225,880, Ser. No. 205,479, and Ser. No. 78,042, each is a continuation-in-part of Ser. No. 18,083, Feb. 24, 1987, Pat. No. 5,041,082, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^5$ .............................................. A61B 17/32
[52] U.S. Cl. .................................... 606/159; 606/170; 604/22
[58] Field of Search .................. 604/22; 606/159, 167, 606/170, 171, 180; 128/772

[56] References Cited

U.S. PATENT DOCUMENTS

| | | | |
|---|---|---|---|
| 3,303,841 | 2/1967 | Dennis | 600/16 |
| 3,403,673 | 10/1968 | MacLeod | 600/16 |
| 4,030,503 | 6/1977 | Clark, III | 606/159 |
| 4,177,797 | 12/1979 | Baylis | 128/754 |
| 4,249,541 | 2/1981 | Pratt | 128/753 |
| 4,456,017 | 6/1984 | Miles | 128/772 |
| 4,627,436 | 12/1986 | Leckrone | 606/159 |
| 4,631,052 | 12/1986 | Kensey | 604/22 |
| 4,706,671 | 11/1987 | Weinrib | 606/159 |
| 4,732,154 | 3/1988 | Shiber . | |
| 4,819,634 | 4/1989 | Shiber . | |
| 4,842,579 | 6/1989 | Shiber . | |
| 4,883,458 | 11/1989 | Shiber . | |
| 4,886,490 | 12/1989 | Shiber . | |
| 4,890,611 | 1/1990 | Monfort | 606/159 |
| 4,894,051 | 1/1990 | Shiber . | |
| 4,923,462 | 5/1990 | Stevens | 606/159 |
| 4,957,482 | 9/1990 | Shiber . | |
| 5,002,553 | 3/1991 | Shiber . | |
| 5,007,896 | 4/1991 | Shiber . | |
| 5,024,651 | 6/1991 | Shiber . | |
| 5,041,082 | 8/1991 | Shiber . | |
| 5,047,040 | 9/1991 | Simpson et al. | 606/159 |
| 5,078,723 | 1/1992 | Dance et al. | 604/22 |
| 5,127,902 | 7/1992 | Fischell | 604/22 |

*Primary Examiner*—Ralph Lewis
*Attorney, Agent, or Firm*—Samuel Shiber

[57] ABSTRACT

An atherectomy system for opening an obstructed vessel comprising a helically shaped flexible guide-wire assembly insertable into the vessel having a cross section which narrows with increasing radial distance from the center of the helical portion, and, a flexible catheter slidable over the flexible guide-wire having a blade at its distal end.

2 Claims, 2 Drawing Sheets

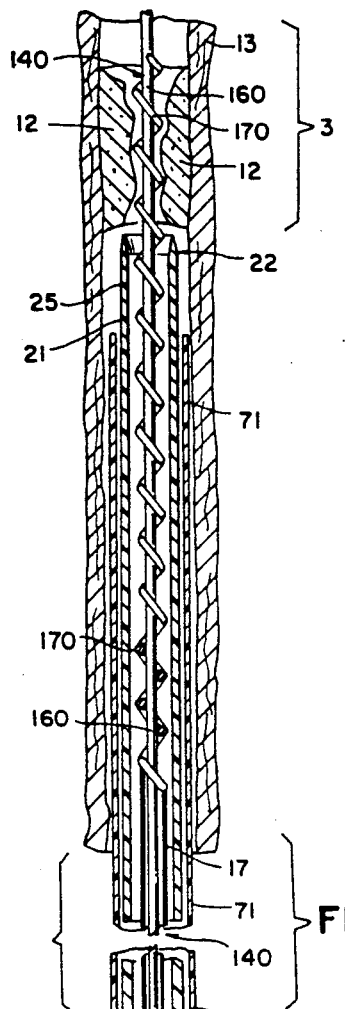
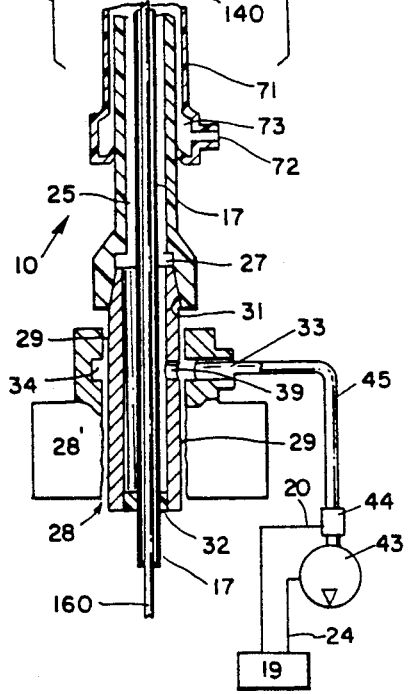
FIG. 2
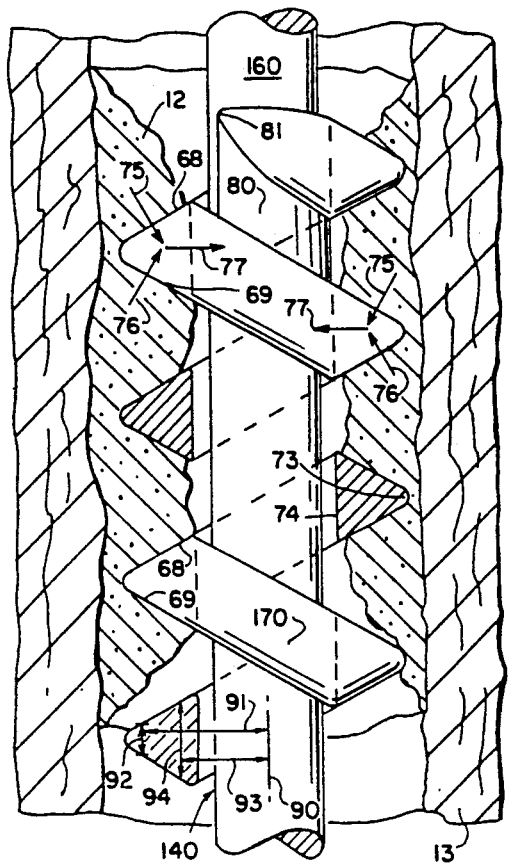
FIG. 3
FIG. 4

LUMEN TRACKING ATHERECTOMY SYSTEM

CROSS REFERENCE TO OTHER APPLICATIONS

This application is a continuation in part of application Ser. No. 07/662,558 filed Feb. 28, 1991 (still pending) which is a continuation in part of application Ser. No. 07/499,726 filed Mar. 27, 1990 now U.S. Pat. No. 5,135,531, which is a continuation in part of application Ser. No. 07/350,020 filed May 12, 1989 now U.S. Pat. No.4,979,939, which is a continuation in part of four applications:

Application Ser. No. 07/326,967 filed Mar. 22, 1989 now U.S. Pat. No. 4,957,482, application Ser. No. 07/324,616 filed Mar. 16, 1989 now U.S. Pat. No. 5,007,896, application Ser. No. 07/323,328 filed Mar. 13, 1989 now U.S. Pat. No. 5,002,553 and application Ser. No. 7/332,497 filed Apr. 03, 1989 now U.S. Pat. No. 5,024,651.

These four applications are continuation in part of application Ser. No. 07/286,509 filed Dec. 19, 1988 now U.S. Pat. No. 4,894,051 which is a continuation in part of application Ser. No. 07/243,900 filed Sep. 13, 1988 now U.S. Pat. No. 4,886,490, which is a continuation in part of three applications:

Application Ser. No. 07/225,880 filed Jul. 29, 1988 now U.S. Pat. No. 4,842,579, application Ser. No. 07/205,479 filed Jun. 13, 1988 now U.S. Pat. No. 4,883,458, and application Ser. No. 07/078,042 filed Jul. 27, 1987 now U.S. Pat. No. 4,819,634.

These three applications are continuation in part of application Ser. No. 07/018,083 filed Feb. 24, 1987 now U.S. Pat. No. 5,041,082 which is a continuation in part of application Ser. No. 06/874,546 filed Jun. 16, 1986 now U.S. Pat. No. 4,732,154 which is a continuation in part of application Ser. No. 06/609,846 filed May 14, 1984 now abandoned.

All the above applications are being incorporated herein by reference.

BACKGROUND AND OBJECTIVES OF THE INVENTION

With age a large percentage of the population develop atherosclerotic obstructions in their blood vessels which diminish circulation and induce serious illnesses such as heart attacks and strokes.

An objective of the present invention is to provide an atherectomy system to open obstructed vessels and a process of performing atherectomy ("atherectomy", as a verb, shall mean the opening of an obstructed vessel by removing and/or displacing material which obstructs a vessel) while externally dilating the vessel to ease in the insertion and extraction of the system, and constricting the vessel to make the atherectomy more effective.

Additionally, alternate dilating and constricting of the vessel, which is synchronized with the patient's own cardiovascular rhythmic pumping, can be used to enhance blood flow in the vessel in order to reduce the risk of clot formation and to improve healing of the vessel and the tissue that it serves.

The above and other objectives of the invention will become apparent from the following discussion and the accompanying drawings.

BRIEF DESCRIPTION OF THE FIGURES

FIG. 2 shows a cross sectioned view of an atherectomy system with a flexible guide wire assembly. The middle portion of the atherectomy system is removed due to space limitations on the drawing sheet.

FIG. 3 shows an enlarged, partially sectioned view of the distal region of the system which is marked 3 on FIG. 2.

FIG. 4 shows an enlarged, partially sectioned end view of the flexible guide wire assembly.

DETAILED DESCRIPTION OF THE DRAWINGS

Figure 1:
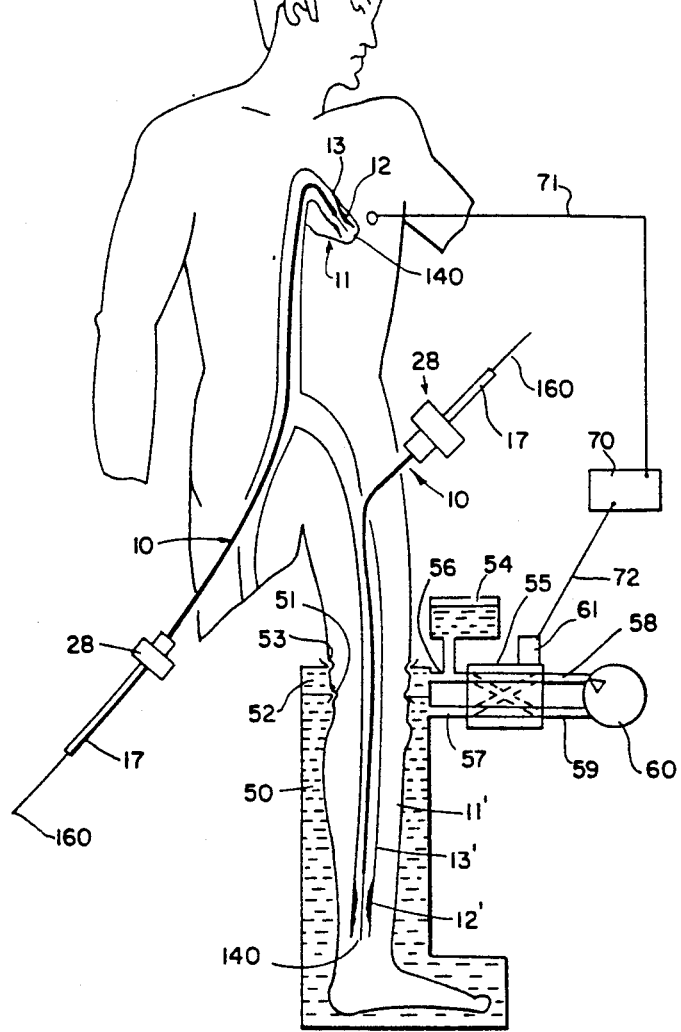
FIG. 1 generally shows one atherectomy system inserted at the groin area, through the skin, through a patient's arterial system, into an obstructed coronary vessel in the patient's heart. A second atherectomy system is inserted at the groin area, through the skin, into an obstructed vessel of a lower leg which is disposed in a vacuum/pressure chamber.

FIG. 1 schematically shows one atherectomy system 10 inserted at the groin area through the skin, through a patient's arterial system, into a coronary vessel 13, in the patient's heart 11, which is obstructed by an obstruction 12. A second atherectomy system 10 (similar parts will be indicated by the same numbers throughout the FIGURES) is inserted at the groin area through the skin, into a vessel 13', in the patient's lower leg 11', which is obstructed by an obstruction 12'. The leg is shown inserted through an opening 53 which seals around the leg, through a secondary chamber 52, through an opening 51 which also seals around the leg and into an adjacent primary chamber 50. The secondary chamber is connected to a sump 54 which is vented to the atmosphere, and to a first port of a solenoid valve 55 by a T shaped conduit 56. The primary chamber is connected to a second port of the solenoid valve by a conduit 57. A pump 60 has its pressure port connected to a third port of the solenoid valve by a conduit 58 and has its suction port connected to a fourth port of the solenoid valve by a conduit 59.

When a solenoid 61 is not energized the solenoid valve internally connects its first port to its third port and its second port to its fourth port, as shown in FIG. 1 in solid lines, and then the pump 60 creates negative pressure in the primary chamber. When the solenoid 61 is energized it causes the valve to cross its internal connections, as shown in FIG. 1 in intermittent lines, and connect port one to port four and port two to port three, and then the pump creates positive pressure in the primary chamber.

When the pump 60 creates negative pressure in the primary chamber it lowers the pressure in the lower leg's tissues which surround the vessel 13', dilating the vessel to ease in the insertion thereto of the flexible guidewire assembly prior to the atherectomy, and it can also be used to ease in the extraction of the system at the end of the procedure. During the atherectomy procedure positive pressure in the primary chamber elevates the pressure in the lower leg's tissues, constricting the vessel, to enhances the procedure's effectiveness by inducing more obstruction material into the atherectomy system. At the end of the procedure negative pressure can be applied to the surrounding tissue in order to dilate the vessel and thereby ease in the extraction of the atherectomy system.

The medium used in the primary and secondary chambers can be gas such as atmospheric air, or if the leg suffers from ulcerating wounds (which often accompany severe atherosclerotic disease) sterilized gas with a high oxygen content and anti bacterial agents may be preferred. Optionally, the chambers can be filled with liquid (for example, lukewarm saline solution) to allow for rapid cycling of alternating negative/positive pressure in the primary chamber, in response to a small volume pumped out/into the chamber at the rate of tens of cycles per minute, without resorting to large and potentially noisy pumps and valves. As the pressure in the primary chamber rises and falls it may create small leakage between the chambers, however, since both chambers contain liquid this does not result in air ingression into the primary chamber or in liquid leaking out of the system. In cases that only gas is used as a medium the secondary chamber can be eliminated to simplify the hardware.

The alternating pressure is produced by a control unit 70 which alternately energizes and de-energizes the solenoid through wires 72. The control unit also monitors, through a wire harness 71 (which is of the type that is used in EKG testing), the patient's own cardiovascular rhythmic pumping of blood and can synchronize the alternating pressure with it to enhance blood flow through the vessel 13'.

The patient's leg may be kept in the primary chamber for a period of time lower the likelihood of blood clots developing in the leg and to assist in the healing of the leg.

FIG. 2 shows the atherectomy system 10 for removing obstruction material 12 from within the patient's vessel 13 which comprises several elongated parts in a nested relationship. The parts' ends will be referred to as "distal" meaning the ends which go further into the vessel and "proximal" meaning the other ends. Thus, "distally" shall indicate a general direction from the proximal end to the distal end, and "proximally" shall refer to an opposite direction.

The atherectomy system comprises:

A flexible guide wire assembly 140 insertable into the vessel.

A flexible catheter 21 slidable over the flexible guide wire assembly, having a blade 22 at its distal end. The flexible catheter defines a passage 25, around the flexible guide wire assembly, for ingesting the obstruction material.

In smaller versions of the system the proximal end of the flexible guide wire assembly is preferably a hollow extension 17 made of a thin walled stainless steel tube, whereas in larger versions the hollow extension is preferably made of a stainless steel wire windings like the catheters shown in my above mentioned U.S. Pat. No. 4,819,634. To the extent that the construction and materials of the helical wire and a structural element of the hollow extension are similar, they can be made integral to reliably and economically form a connection between the helical wire and the hollow extension.

The hollow extension and the helical wire are both slidable over the flexible guide wire 160 which can be a commercially available standard guide wire. Bio-compatible coatings or lubricants may be disposed on the various parts of the flexible guide wire assembly, to ease their motion relative to the obstructed vessel or to one another, and to prevent blood clots from developing around them. A helical void is defined between the coils of the helical wire 170 for containing and holding the obstruction material.

Coupling means in the form of a conical seat 27 couples the flexible catheter to a drive means in the form of a motor assembly 28 having the hollow shaft 29 with a matching tapered end 31 and a seal 32 at its other end. The helical wire 170 takes up the free play between the flexible guide wire 160 and the flexible catheter 21, concentrically aligning one with the other. A void defined between the helical wire's coils serves to hold the obstruction material during the atherectomy and to restrain the cut obstruction material from freely rotating around the flexible guide-wire, and to the extent that the obstruction material is frictionally rotated by the flexible catheter, this rotation is translated by the helical wire to urge the cored obstruction material proximally in the passage.

Optional suction is applied to the passage 25 by an adaptive suction system, through a port 33 which communicates with a groove 34 defined by a motor assembly's housing 28', which communicates with hole 39, which communicates with a hollow shaft 29, which communicates with the proximal end of the passage 25. The suction is provided by a motor and pump assembly 43 with the motor being, preferably, a variable speed motor, and with the pump being, preferably, a positive displacement pump such as a piston pump or a peristalic pump, which limits the amount of blood removed through the passage in the flexible catheter to the volume that is displaced by the pump. When only blood is flowing in the passage and trough a conduit 45 the negative pressure in the conduit 45 is low. When obstruction material enters the passage a higher negative pressure is needed to pull it proximally, and as the negative pressure increases the leakage and volumetric losses in the pump increase, leaking to a diminished flow through the conduit 45. A signal corresponding to the diminished flow is generated by a flow sensor 44, which is installed in the conduit 45, and this signal is transmitted to the control unit 19 via wires 20, and the unit 19 responds, through wires 24, by increasing the pumping rate of assembly 43 to make up for these higher volumetric losses. As soon as the obstruction particles pass through the atherectomy system and the resistance to flow through the conduit decreases, the flow rate increases, and the flow sensor transmits to the control unit a corresponding signal which causes the control unit to decrease the pumping rate of assembly 43 in order to avoid excessive removal of blood from the patient.

A flexible sleeve 71 is used to introduce the flexible catheter into the vessel and direct it to the obstruction's site. A nipple 72 which is connected to the flexible sleeve through an annular chamber 73 can be used for fluid delivery into the vessel.

FIG. 3 shows an enlarged, partially sectioned view of the distal region of the system which is marked 3 on FIG. 2. The helical wire 170 has a trapezoidal shaped cross-section. The term "trapezoidal shaped cross-section", as used herein, means a cross-section which narrows in width with increasing radial distance from the center of the helical portion. For example, the width of the cross-section (widths and distances are shown by means of double arrowed lines which are in turn marked by numerals) is 94 at a radial distance 93 from the center of the helical portion which is marked by line 90 and the width of the cross-section narrows to 92 at a radial distance 91.

Since the cross-section's narrow side 73 is on the outer periphery of the helical wire it is sunken deeper into the obstruction material than the wide side 74, as illustrated in FIG. 3. Forces which develop between the displaced obstruction material and the helical wire against side surfaces of the trapezoidal cross section, 68 and 69, are illustrated by arrows marked 75 and 76, respectively, and the resultant of these forces is a radial force marked 77 which urges the helical wire towards the center of the lumen, urging the helical wire and subsequently the flexible catheter, to track, and thereby stay in the lumen. In addition, the deeper layers of obstruction material, which are closer to the wall of the vessel 13, are older and tend to be harder and since the trapezoidal cross-section displaces less of this harder layer the overall resistance to the threading of the helical wire through the obstruction is reduced, compared to, for example, a helical wire with a round or a square cross section.

To prevent the helical wire from entangling with the flexible guide wire the distal entry to the void between its coils is partially closed by a thin arcuate gate 80 which is preferably made from radio opaque material to enhance its visualization when viewed using X ray equipment.

FIG. 4 shows an enlarged, partially sectioned end view of the flexible guide wire assembly with the flexible guide wire 160, the helical wire 170, the gate 80 and the sharpened distal tip 81 of the helical wire.

Figure 5:
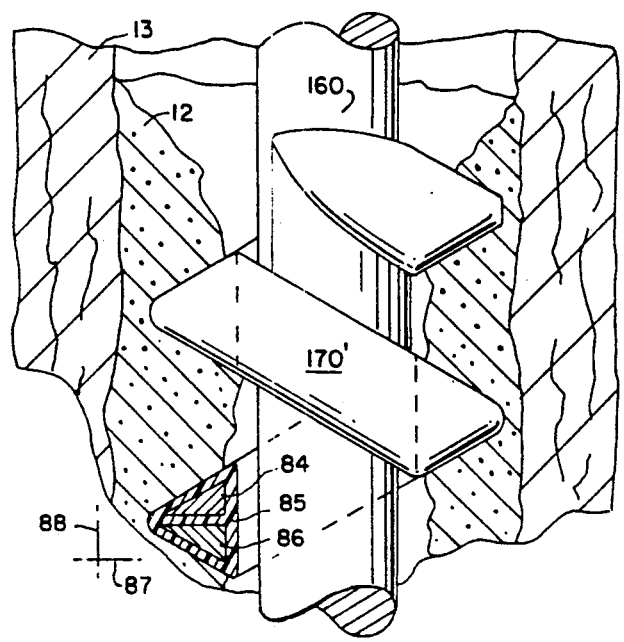
FIG. 5 shows an enlarged, partially sectioned view of the distal region of the system which is marked 3 on FIG. 2, which utilizes a modified helical wire having a trapezoidal cross section.

FIG. 5 shows an enlarged, partially sectioned view of the distal region of the system which is marked 3 on FIG. 2, which utilizes a modified helical wire 170' made of two layers 84 and 86 which individually have a triangular cross-section. The two layers are encapsulated together in a plastic jacket 85, forming together a trapezoidal shaped cross-section. The plastic jacket makes the two layers thread through the obstruction material as one piece but it is sufficiently flexible not to effect their cross-section modulus. Thus the multi layer construction has a substantially lower cross-section modulus around their neutral axis which is parallel to axis 87 as compared with a similarly sized non-layered cross-section shown in FIG. 3, but it has a minimal effect on the cross-section modulus around the neutral axis which is parallel to axis 88. This improves the helical wire's ability to conform to the vessel's curves with a minimal loss in its torque carrying capacity which is needed for threading it through the obstruction material.

OPERATION

A process for performing atherectomy comprising the following steps:

Dilating the obstructed vessel by applying negative pressure to surrounding tissue by means such as the primary chamber 50 and associated means shown in FIG. 1. Inserting into the vessel the distal portion of the flexible guide wire assembly 140 and engaging the obstruction material by threading the helical wire 170 into it.

Before starting to form the lumen with the flexible catheter the negative pressure applied to the surrounding tissues is replaced with a positive pressure which constricts the vessel and urges the obstruction material onto the helical wire.

Sliding and distally advancing the flexible catheter 21 over the flexible guide wire assembly to form a lumen through the obstructed vessel.

After the flexible catheter forms the lumen the pressure which was applied to the tissue surrounding the vessel to constrict it is removed and optionally replaced with a negative pressure to again dilate the vessel and ease in the extraction of the system.

Finally, the chamber primary 50 and the associated means shown in FIG. 1, can be used to enhance blood flow through the vessel alternating the pressure in the chamber 50 in synchronization with the patient's cardiovascular system. Such blood flow enhancement can reduce the likelihood of a blood clot forming in the vessel and improve the healing of the leg by providing more nutrients through improved circulation.

While the present invention has been illustrated by a limited number of embodiments, it should be understood that various modifications and substitutions may be made without departing from the spirit of the invention or the scope of the claims.

I claim:

1. An atherectomy system for opening an obstructed vessel, comprising in combination:
    flexible guide-wire assembly insertable into the vessel, at least a portion of which is made of a helical wire having a trapezoidal shaped cross-section which narrows in width with increasing radial distance from the center of the helical portion, and,
    a flexible catheter, slidable over said flexible guide-wire assembly, having a blade at its distal end.

2. An atherectomy system as in claim 1, said helical wire is made of a layered construction.

* * * * *